(12) United States Patent
Charles et al.

(10) Patent No.: US 7,235,405 B2
(45) Date of Patent: Jun. 26, 2007

(54) LIQUID PRODUCT DISTRIBUTION DEVICE AND METHOD

(75) Inventors: Raymond Charles, Sean de Moirans (FR); Yves Fouillet, Voreppe (FR); Nicolas Sarrut, Seyssinet (FR); Patricia Claustre, Joiraus (FR)

(73) Assignee: Commissariat A l'Energie Atomique, Paris (FR)

( * ) Notice: Subject to any disclaimer, the term of this patent is extended or adjusted under 35 U.S.C. 154(b) by 623 days.

(21) Appl. No.: 10/426,895

(22) Filed: Apr. 29, 2003

(65) Prior Publication Data

US 2004/0022686 A1    Feb. 5, 2004

(30) Foreign Application Priority Data

May 7, 2002    (FR) .................................. 02 05716

(51) Int. Cl.
*G01N 1/10* (2006.01)
(52) U.S. Cl. .................... 436/180; 422/81; 422/82; 422/100; 436/52; 436/53; 436/180
(58) Field of Classification Search ................ 422/81, 422/82, 100; 436/52, 53, 180
See application file for complete search history.

(56) References Cited

U.S. PATENT DOCUMENTS 3,726,297 A    4/1973    Heimann et al.
4,015,938 A    4/1977    Jay
4,294,800 A  * 10/1981  Tavlarides et al. ............ 422/50
5,766,959 A  *  6/1998  Dasgupta ..................... 436/174

FOREIGN PATENT DOCUMENTS

| EP | 0 377 202 A2 | 7/1990 |
| EP | 1 002 570 A1 | 5/2000 |
| GB | 2 359 765 A | 9/2001 |

* cited by examiner

*Primary Examiner*—Jan M. Ludlow
(74) *Attorney, Agent, or Firm*—Thelen Reid Brown; Raysman & Steiner LLP

(57) ABSTRACT

The invention relates to a device (1) for distribution of at least one liquid product, the device comprising at least one injection tube (2) supplied by a liquid product and being provided with an outlet orifice (4) capable of cooperating with an inlet orifice (12) of a reception tube (10) for reception of each liquid product. According to the invention, the outlet orifice (4) of each injection tube (2) and the inlet orifice (12) of the reception tube (10) open up into a sealed reservoir (6) full of an immiscible liquid (8), the outlet orifice (4) of each injection tube (2) being at a spacing from the inlet orifice (12) of the reception tube (10) and able to be located close to the reception tube (12), the device (1) also comprising means (14) for pressurizing the immiscible liquid (8).

19 Claims, 3 Drawing Sheets

LIQUID PRODUCT DISTRIBUTION DEVICE AND METHOD

CROSS-REFERENCE TO RELATED APPLICATION

This application claims priority based on French Application No. 02 05716, entitled "Liquid Product Distribution Device And Method" by Raymond Charles, Yves Fouillet, Nicolas Sarrut and Patricia Claustre, filed on May 7, 2002, and which was not published in English."

DESCRIPTION

1. Technical field

This invention relates to a device for distribution of at least one liquid product, the device comprising at least one injection tube supplied by a liquid product and being provided with an outlet orifice capable of cooperating with an inlet orifice of a reception tube for reception of each liquid product.

More specifically, the invention relates to a device for distribution of several liquid products, the distribution being made such that liquid products are ejected from the device in low quantities, in sequence, in a determined order.

This invention also relates to a method for distribution of at least one liquid product, the method potentially being used through such a distribution device.

2. State of Prior Art

Several embodiments have already been proposed in this technical field.

Conventional multi-way valves are known for use for the distribution of several liquid products. This type of valve usually comprises several injection tubes, each supplied with a different liquid product and preferably an immiscible product, and a single reception tube that can cooperate with each of the injection tubes, in sequence and in a determined order. In this way, the reception tube comprises several liquid products inside it, also called a "plugs stream", and these liquid products can be ejected from the valve in a determined order in which the reception tube will cooperate with the various injection tubes of the valve.

However, there are serious disadvantages with the use of such a multi-way valve. The mobile part of this valve enabling cooperation between a given injection tube and the reception tube is brought into contact in sequence with each of the liquid products to be ejected. Thus, when moving from a first to a second injection tube, the mobile part of the multi-way valve can transport a small quantity of liquid product from the first injection tube leading towards the second injection tube, and thus create a mix with the liquid product located in the second injection tube. Following the repetition of movements of the mobile part of the valve between the different injection tubes, the liquid products located in these tubes mix with each other, obviously to the detriment of their purity.

Furthermore, the use of a multi-way valve does not always enable the injection of small quantities of liquid products. This is made impossible due to the presence of large dead volumes in multi-way valves, normally making it impossible to inject quantities smaller than one milliliter.

T connectors are also known in prior art, consisting of two injection tubes each supplied by an immiscible liquid, and a reception tube capable of collecting a plugs stream composed of an alternation of two immiscible liquid products.

However, this type of connector has a relatively limited operating speed. Furthermore, T connectors are very sensitive to the presence of gas inside liquid products. When one of two liquid products contains gas bubbles and is injected into the reception tube, the presence of gas bubbles sometimes tends to force a small quantity of liquid product to rise up into the connector, consequently coming into contact with the other liquid product, and thus causing contamination of the other liquid product.

PRESENTATION OF THE INVENTION

Thus, the object of the invention is to propose a device for the distribution of at least one liquid product, the device comprising at least one injection tube supplied with a liquid product and comprising an outlet orifice capable of cooperating with an inlet orifice of a reception tube for reception of each liquid product, the device also at least partially correcting the disadvantages mentioned above related to embodiments according to prior art.

More precisely, the purpose of the invention is to propose a device for distribution of at least one liquid product, for which operation is not disturbed in any way by the presence of a gas inside said liquid product(s) to be distributed, and for which the design specifically prevents mixing of several liquid products in the same injection tube.

Furthermore, another object of the invention is to present a method for distribution of at least one liquid product, the method being useable through a distribution device satisfying the object mentioned above.

In order to achieve this, the first object of the invention is a device for distribution of at least one liquid product, the device comprising at least one injection tube supplied with a liquid product and comprising an outlet orifice that can cooperate with an inlet orifice of a reception tube for reception of each liquid product. According to the invention, the outlet orifice of each injection tube and the inlet orifice of the reception tube open up into a sealed reservoir full of an immiscible liquid, the outlet orifice of each injection tube being at a spacing from the inlet orifice of the reception tube and able to be located close to the reception tube, the device also comprising means for pressurizing the immiscible liquid.

Advantageously, with this arrangement in which liquids to be distributed may be added into injection tubes by pressurization or injection of defined volumes, the distribution device according to the invention avoids contact between the different liquid products located in their corresponding injection tubes and is largely insensitive to the presence of gas bubbles in these liquid products.

When a liquid product is injected from an arbitrary injection tube, a drop of liquid product is formed and projects into the reservoir full of an immiscible liquid, in which the product drop is confined and grows until it comes into contact with the inlet orifice of the reception tube, so as to form a liquid bridge between these two tubes. Note that when the number of injection tubes is not equal to one, it is advantageous to provide the outlet orifice of each injection tube with drop guidance means so that the drop is guided towards the direction of the reception tube inlet orifice. These guidance means thus prevent the drop formed from coming into contact with injection tube outlet orifices located nearby, rather than with the inlet orifice of the reception tube as is essential for correct operation of the device according to the invention.

After the drop has been formed between the two orifices, the immiscible liquid is pressurized making the liquid product drop to be detached and pushed towards the inside of the reception tube. In this way, if the liquid product injected into the tube has any gas bubbles in it, the gas bubbles can escape into the reservoir, along the space provided between the injection tube and the reception tube, without causing displacement of the liquid product injected to another injection tube.

Furthermore, the distribution device according to the invention has an immiscible liquid as an element that will create a passageway between a given injection tube and the reception tube. Consequently, this specific property of the invention minimizes the risks of mixing between the different liquid products to be distributed, in the sense that unlike the phenomenon encountered when a mobile element of a multi-way valve is used, no residue of the liquid product being injected remains attached to the immiscible liquid. Therefore the entire volume of the injected liquid product is transferred inside the reception tube, which consequently prevents any contact between the injected liquid product and another injection tube used later.

Furthermore, the lack of contact between the different liquid products may be further reinforced, if pressurization of the immiscible liquid is stopped only after adding an entire drop of liquid product into the reception tube followed by a small quantity of immiscible liquid.

By proceeding in this way, the part of the immiscible liquid that participated in confinement of the product drop between the injection tube and the reception tube is also injected into the reception tube, such that said drop can no longer come into contact with a liquid product located in another injection tube. Furthermore, another advantage related to the presence of the immiscible liquid inside the reception tube is that a plugs stream can be obtained in which different liquid products are separated from each other by means of the immiscible liquid, thus preventing any mix between the liquid products inside the reception tube.

Preferably, the distribution device comprises at least two injection tubes at a distance from each other and supplied by different liquid products, the injection tubes possibly cooperating with the device reception tube, in sequence and in a determined order.

According to a first preferred embodiment of this invention, each of the injection tube outlet orifices is close to the inlet orifice of the reception tube of the device. Obviously, this means that the design of the device can be relatively simple, and that it can operate at high speeds.

According to a second preferred embodiment of this invention, each injection tube may be displaced such that its outlet orifice is close to the inlet orifice of the reception tube of the device. This proposed solution advantageously enables the use of a large number of injection tubes and consequently results in obtaining a plugs stream composed of a wide variety of liquid products.

Preferably, the injection tubes are then placed on a tube support that can be moved in translation and/or rotation with respect to the reception tube of the device.

According to a third preferred embodiment of this invention, the reception tube of the device may be moved so that its inlet orifice is close to the outlet orifice of a determined injection tube.

It is also possible to use a micro-tube as the injection tube for the three preferred embodiments, for example capable of injecting less than 1 milliliter of a liquid product into the reception tube.

Also advantageously, the distribution device comprises means for analyzing a drop or a liquid bridge located between the outlet orifice of an injection tube and the inlet orifice to the reception tube of the device, these analysis means being preferably fluorescence detection means.

Another purpose of the invention is a method for distributing at least one liquid product, the method being useable through a distribution device like that defined in the invention and described above. The method according to the invention consists of reiterating the following steps:
  injection of a liquid product from an injection tube in order to form a drop of a liquid product projecting outside the injection tube and coming into contact with the inlet orifice of the reception tube of the device;
  pressurization of the immiscible liquid located inside the sealed reservoir to detach the drop of liquid product from the injection tube outlet orifice and to push the drop inside the reception tube of the device.

According to one preferred embodiment, the liquid product injecting step causing the formation of the drop in contact with the outlet orifice of the injection tube and the inlet orifice of the reception tube, is followed by a step in which liquid product is poured from the injection tube towards the reception tube passing through the drop, which forms a liquid bridge between the two tubes.

Consequently, it is possible to make injections of very large volumes of liquid products, much greater than the volume of the drop forming the liquid bridge between the injection tube and the reception tube of the device.

Other advantages and characteristics of the invention will become clear after reading the detailed non-limitative description given below.

BRIEF DESCRIPTION OF THE DRAWINGS

This description will be made with reference to the attached drawings among which.

DETAILED DESCRIPTION OF PREFERRED EMBODIMENTS

Figure 1:
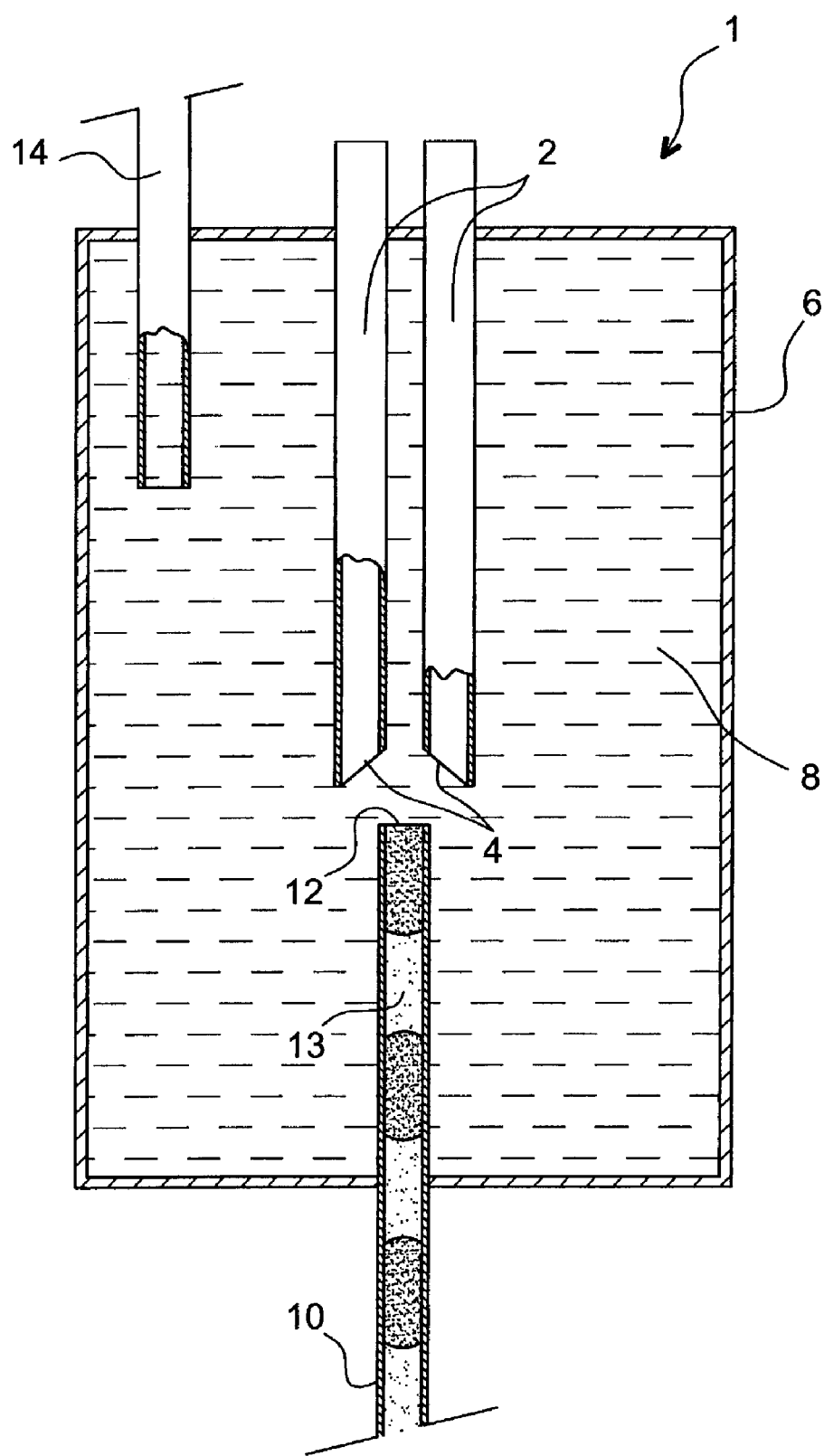
FIG. 1 shows a diagrammatic view of a distribution device according to a first preferred embodiment of this invention.

FIG. 1 illustrates a device 1 for distribution of at least one liquid product according to a first preferred embodiment of this invention.

In this preferred embodiment, the device 1 comprises two injection tubes 2 separated from each other and approximately parallel to each other, along an approximately vertical direction. Obviously, the device 1 could contain more injection tubes 2 without going outside the scope of the invention. Each injection tube 2 is provided with a corresponding outlet orifice 4 at the bottom end visible in FIG. 1, these output orifices 4 opening up inside a sealed reservoir 6 filled with an immiscible liquid 8, preferably composed of oil. Note that each of the injection tubes 2 may be supplied with a different liquid product, and that these tubes 2 are preferably micro-tubes with an inside diameter appropriate to the characteristics of the liquid product used, such as the viscosity or the surface tension, so that a drop or a liquid bridge will form at the outlet orifice 4 from the injection tube 2. Thus, the device 1 according to the invention may be used on very small-scale systems such as biochips, "lab-on-a- chip" or other microfluidic devices. Valves or injection systems (not shown) are placed in each of the tubes 2, to selectively control the distribution of each liquid product.

The distribution device 1 also comprises a reception tube 10, approximately vertical, for which an inlet orifice 12 corresponding to its upper end visible in FIG. 1, also opens up in the sealed reservoir 8. A plugs stream 13 consisting of an alternating stack of small volumes of two liquid products originating from injection tubes 2, is located inside the reception tube 10 so that it can be continuously ejected from device 1.

In this embodiment, the injection tubes 2 and the reception tube 10 are fixed and positioned such that each outlet orifice 4 is at a spacing from the inlet orifice 12, and that each of these outlet orifices 4 is located close to the inlet orifice 12 of the reception tube 10.

As can be seen in FIG. 1, the proximity of the different orifices 4 and 12 may be achieved by arranging the reception tube 10 approximately underneath and between the two injection tubes 2. Note also that the injection tube 2 and the reception tube 10 are placed approximately parallel to each other in the same plane. Furthermore, the outlet orifices 4 from the injection tubes 2 are each provided with drop guidance means, such that its enlargement takes place in the direction of the inlet orifice 12 of the reception tube 10, and not in the direction of an outlet orifice 4 from another injection tube 2. In the preferred embodiment described, these drop guidance means are in the specific shape of the outlet orifice 4, which is beveled so that it is facing slightly towards the inlet orifice 12 of the reception tube 10. Furthermore, note that these guidance means may also be in the form of a wire connecting orifices 4 and 12, or a protuberance or any other form that can contribute to drawing, confining or deforming the drop.

The device 1 also comprises means for pressurizing the immiscible liquid 8, particularly consisting of an inlet 14 of immiscible liquid 8 that can be opened in order to make liquid 8 penetrate inside the sealed reservoir 6, and consequently increase the pressure inside this reservoir.

FIGS. 2a to 2d contain diagrammatic views symbolically showing the operating principle of the distribution device 1 according to the first preferred embodiment of the invention.

As already mentioned above, the liquid products forming the plugs stream 13 originate from injection tubes 2, and the injection tubes cooperate in turn with the reception tube 10.

Figure 2D:
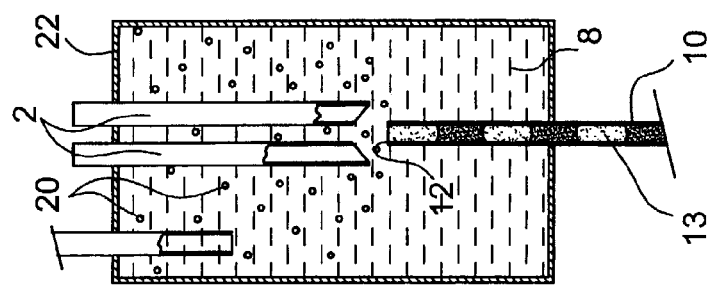
FIGS. 2a to 2d show diagrammatic views symbolically showing the operating principle of the distribution device shown in FIG. 1, showing details of how the liquid product passes from one injection tube to the reception tube in the device.
Figure 2C:
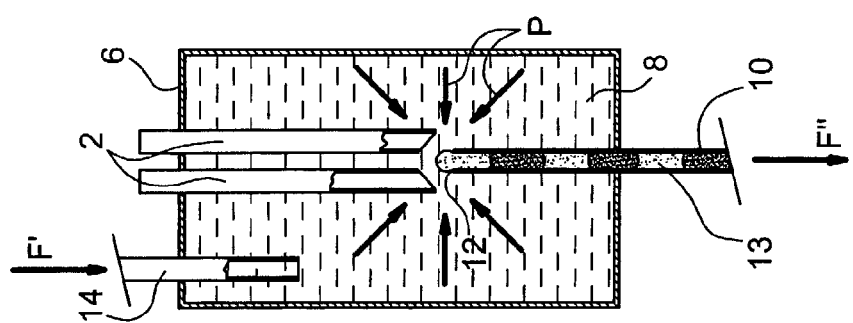
Figure 2B:
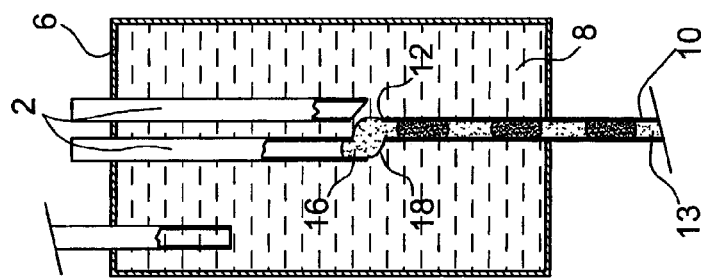
Figure 2A:
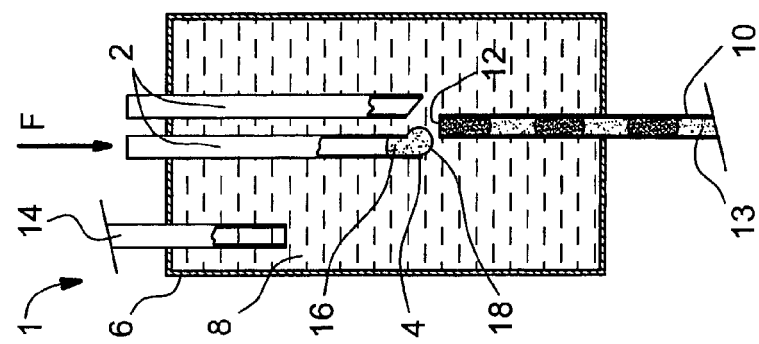

When a determined volume of liquid product 16 has to be injected into the reception tube 10 to reach the plugs stream 13, the valve or the syringe, or syringe pusher, or pump type of injection system fitted on the injection tube 2 allows the determined volume of liquid product to pass towards the outlet orifice 4, as shown by the arrow F in FIG. 2a. Naturally, the inlet 14 of the means for pressurizing the immiscible liquid 8 is closed during injection of the liquid product 16 into the sealed reservoir 6.

A drop 18 of liquid product 16 then begins to form as it projects out of the injection tube 2, this drop 18 being confined by the immiscible liquid 8 present inside the sealed reservoir 6. Note that the drop 18 remains fixed to the outlet orifice 4 of the injection tube 2, by capillarity.

As injection of the liquid product 16 is continued, the drop 18 becomes larger until it comes into contact with the inlet orifice 12 of the reception tube 10, so as to create a liquid bridge between the two tubes 2 and 10. Note that as soon as the drop 18 stabilizes as it comes into contact with the inlet orifice 12, the liquid 16 may also begin to go down in the reception tube 10, without activating the pressurization means of the immiscible liquid 8.

Injection of the liquid product 16 stops when practically the entire determined volume of this product 16 is in the drop 18 as shown diagrammatically in FIG. 2a which shows the state in which the drop 18 is stable. A relatively small proportion of the determined volume of the liquid product 16 is present at any one time in the injection tube 2 and in the reception tube 10, to enable the drop 18 to be fixed to the and inlet outlet orifices 4 and 12.

According to a preferred embodiment of this invention, it is also possible to ensure that when the drop 18 forms a liquid bridge between the two tubes 2 and 10, a liquid flow 16 takes place from the injection tube 2 towards the reception tube 10, such that the quantity of liquid product 16 injected into the reception tube 10 passing through the liquid bridge is greater than the simple volume of the drop 18. Thus, continuous injections of very large industrial type volumes can be made from any injection tube 2 to the reception tube 10 of the device 1, passing through the drop 18 forming the liquid bridge between the two tubes 2 and 10.

Then, when the drop 18 has come into contact with the inlet orifice 12 of the reception tube 10 to form the liquid bridge, or when the flow of product 16 passing across the liquid bridge formed towards the reception tube 10 is completed, the immiscible liquid 8 is pressurized. This is achieved by opening the inlet 14 and adding a determined quantity of immiscible liquid 8 inside the sealed reservoir 6. The addition of the determined quantity of immiscible liquid 8 is shown symbolically by the arrow F' in FIG. 2c, which also represents the pressure applied on the drop or the liquid bridge 18 through arrows P.

The injection tube 2 in contact with the drop 18 is then closed off at its end opposite the end including the outlet orifice 4, the pressure P distributed around the drop 18 draws it towards the inside of the reception tube 10, which is open at its two ends. The result is that the drop or the liquid bridge 18 is detached from the outlet orifice 4 of the injection tube 2, and that a liquid product 16 forming the drop 18 is added inside the reception tube 10. The liquid product 16 then joins the plugs stream 13 that already exists and forces it to move outside the device 1 as shown by the arrow F".

With reference to FIG. 2d, pressurization of the immiscible liquid 8 is stopped by closing the inlet 14 of the device 1. This closure is done when the determined volume of liquid product 16 has all been added into the reception tube 10. Furthermore, note that this closure may also take place only when a small quantity of immiscible liquid 8 has been added into the reception tube 10, thus creating a separation between each volume of liquid product in the plugs stream 13.

Still with reference to FIG. 2d, it can be seen that when the liquid product 16 contains gas bubbles 20, they may escape in the sealed reservoir 6 towards a surface 22 of the reservoir, following the space between the outlet orifice 4 of the injection tube 2, and the inlet orifice 12 of the reception tube 10.

All the operations that have just been described to transfer a determined volume of liquid product 16 from one of the injection tubes 2 to the reception tube 10, are then reiterated with the other reception tube 2 containing a different liquid product. The injection tubes 2 and the reception tube 10 cooperate alternately one after the other almost continuously, so as to obtain a continuous ejection of the plugs stream 13 outside the device 1.

Liquid products are injected into the injection tubes 2 and the immiscible liquid inlet 14 is opened/closed under the control of an electronic, mechanical, pneumatic or manual control unit (not shown), connected to the distribution device 1. Note that with this type of control unit, it is easy to program injection speeds and the value of volumes of liquid products to be injected, these data directly controlling the distribution speed of the plugs stream 13 outside the device 1.

Figure 3:
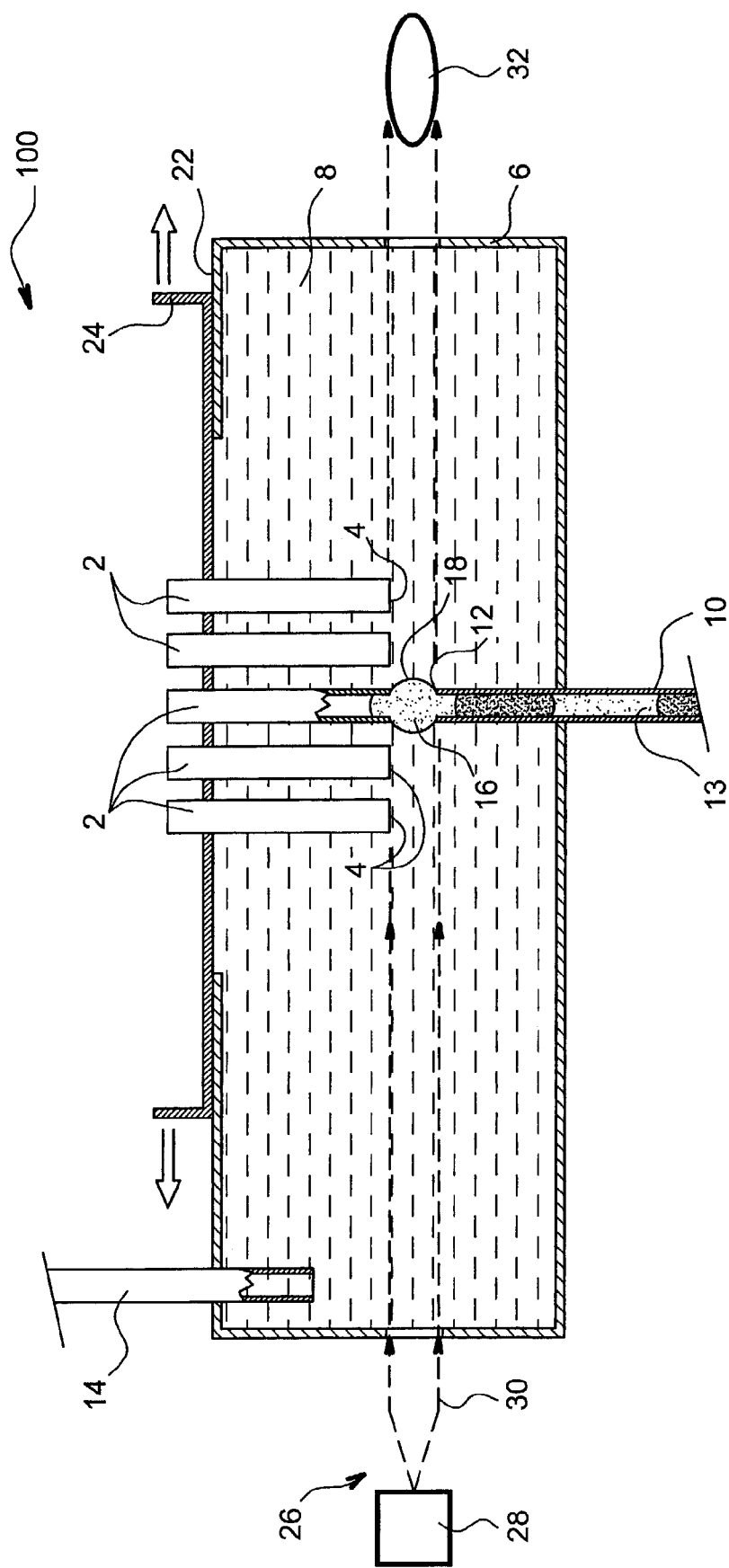
FIG. 3 shows a diagrammatic view of a distribution device according to a second preferred embodiment of this invention.

According to a second preferred embodiment of this invention with reference to FIG. 3, the figure shows a device 100 for distributing several liquid products.

As in the preferred embodiment described above, the distribution device 100 comprises several approximately vertical injection tubes 2, each provided with an outlet orifice 4. The outlet orifice 4 corresponding to the lower ends of the tubes 2 that can be seen in FIG. 3 each open up into a sealed reservoir 6 filled with an immiscible liquid 8, preferably composed of oil.

Similarly, the distribution device 100 also comprises an approximately vertical reception tube 10, of which a horizontal inlet orifice 12, corresponding to its upper end that can be seen in the figure, also opens up into the sealed reservoir 8. A plugs stream 13 consisting of an alternating stack of small volumes of liquid products originating from injection tubes 2, is located inside the reception tube 10 so that it can be ejected continuously from the device 100.

Finally, the device 100 also comprises means for pressurizing the immiscible liquid 8, particularly composed of an inlet 14 of immiscible liquid 8 that can be opened in order to make the liquid 8 penetrate inside the sealed reservoir 6, and consequently generate an increase of pressure inside this reservoir.

Unlike the distribution device 1 in the first preferred embodiment of this invention, the device 100 comprises several injection tubes 2 placed on a mobile tube support 24. The injection tubes 2 are placed adjacent to each other and approximately parallel to each other in the tube support 24, the tube support being moved in translation and/or in rotation with respect to the reception tube 10 fixed mounted on the sealed reservoir 6. Thus, when the plugs stream 13 has to be terminated by a specific liquid product 16, the tube support 24 is moved to make the injection tube 2 supplied by the liquid product 16 move, such that the outlet orifice 4 of this tube 2 is located close to the inlet orifice 12 of the reception tube 10.

Once the displacement of the injection tube 2 is done, this displacement preferably moves the outlet orifice 4 of this tube 2 into a position facing the inlet orifice 12 of the reception tube 10, and the operations to transfer the liquid product 16 described above and illustrated in FIGS. 2a to 2d can be done in exactly the same way.

A control unit (not shown) that may be electronic, mechanical, pneumatic or manual, can then put the successive placements of the different orifices 4 and 12 into order, so that the injection tubes 2 cooperate with the reception tube 10 in sequence and in a predetermined order programmed in the control unit. Note that the control unit designed to manage displacements of the injection tubes 2 may also control the injection speeds and the value of the volumes of the liquid products to be injected.

As can be seen in FIG. 3, the device 100 also comprises means 26 for analyzing the drop 18 or the liquid product bridge 16, this drop 18 being located between the outlet orifice 4 of the injection tube 2 and the inlet orifice 12 of the reception tube 10. Preferably, the analysis means 26 are fluorescence detection means composed of a light source 28 generating a light beam 30 passing across the sealed reservoir 6, passing through the space between the outlet orifice 4 of the injection tube 2 and the inlet orifice 12 of the reception tube 10. After passing across the sealed reservoir 6, the light beam 30 is projected onto a fluorescence reception screen 32. The drop 18 can then be analyzed, depending on the nature of the fluorescence reception.

According to a third preferred embodiment of this invention (not shown), the distribution device is designed so that the reception tube can move with respect to several injection tubes placed approximately parallel to each other and adjacent to each other, and installed fixed on the sealed reservoir of the device. Thus, the mobility of the reception tube enables the reception tube 2 to bring its inlet orifice close to the outlet orifice of a determined injection tube, as a function of the liquid product that will join the plugs stream of the device.

As in the second preferred embodiment of the invention, the reception tube may be moved in translation and/or in rotation with respect to the injection tubes of the device.

Obviously, a person skilled in the art can make various modifications to the distribution devices 1 and 100 described above, which are simply given as non-limitative examples.

The invention claimed is:

1. Device for distribution of at least one liquid product, said device comprising:
   at least one injection system;
   at least one injection tube supplied with a liquid product by the at least one injection system, and being provided with an outlet orifice, said injection tube being adapted to form a drop of the liquid product projecting outside thereof;
   a reception tube configured to receive the drop of each liquid product and being provided with an inlet orifice, wherein the outlet orifice of each injection tube is configured to cooperate with the inlet orifice of the reception tube, and the outlet orifice and the inlet orifice open up into a sealed reservoir filled with an immiscible liquid, the outlet orifice of each injection tube being at a spacing from the inlet orifice of the reception tube and able to be located to the vicinity of the reception tube;
   means for pressurizing the immiscible liquid; and
   a control unit coupled to the at least one injection system and the means for pressurizing,
   wherein the control unit, at least on injection system, and means for pressurizing are operative to form a drop of said liquid product projecting outside of the at least one injection tube and coming into contact with the inlet orifice of the reception tube and to pressurize the immiscible liquid inside the sealed reservoir to detach the drop of liquid from the at least one injection tube and to push the drop inside the reception tube.

2. Device for distribution according to claim 1, wherein said device comprises at least two injection tubes positioned at a distance from each other and supplied with different liquid products, the injection tubes being adapted to cooperate with the reception tube of the said device, in sequence and in a determined order.

3. Device for distribution according to claim 2, wherein each of the outlet orifices of the injection tubes is located in the vicinity of the inlet orifice of the reception tube of said device.

4. Device for distribution according to claim 3, wherein the outlet orifice of each of the injection tubes is provided with guidance means for a drop of the liquid product to be distributed, such that the drop forms between said outlet orifice and the inlet orifice of the reception tube.

5. Device for distribution according to claim 2, wherein each injection tube is moveable such that its outlet orifice is placed in the vicinity of the inlet orifice of the reception tube of said device.

6. Device for distribution according to claim 5, wherein the injection tubes are placed on a tube support movable in translation and/or rotation with respect to the reception tube of said device.

7. Device for distribution according to claim 2, wherein the reception tube of said device is movable so that its inlet orifice is placed in the vicinity of the outlet orifice of a determined injection tube.

8. Device for distribution according to claim 1, wherein each injection tube is a micro-tube.

9. Device for distribution according to claim 1, wherein the immiscible liquid located inside the sealed reservoir is oil.

10. Device for distribution according to claim 1, further comprising:
   means for analyzing a drop of the liquid product located between the outlet orifice of an injection tube and the inlet orifice of the reception tube of said device.

11. Device for distribution according to claim 10, wherein said analysis means are fluorescence detection means.

12. Device for distribution according to claim 1, wherein said device is configured to be implemented in a biochip or a microfluidic device.

13. Device for distribution according to claim 1, wherein said means for pressurizing the immiscible liquid is adapted to detach the drop of liquid product from the outlet orifice of the injection tube and to push the drop inside the reception tube.

14. Method for distributing at least one liquid product through a distribution device comprising:
   at least one injection tube supplied with a liquid product and being provided with an outlet orifice, said injection tube being adapted to form a drop of the liquid product projecting outside thereof;
   a reception tube configured to receive the drop of each liquid product and being provided with an inlet orifice, wherein the outlet orifice of each injection tube is configured to cooperate with the inlet orifice of the reception tube, and the outlet orifice and the inlet orifice open up into a sealed reservoir filled with an immiscible liquid, the outlet orifice of each injection tube being at a spacing from the inlet orifice of the reception tube and able to be located to the vicinity of the reception tube; and
   means for pressurizing the immiscible liquid, said method comprising:
   injecting a liquid product from the injection tube, in order to form a drop of said liquid product projecting outside the injection tube and coming into contact with the inlet orifice of the reception tube of said device; and
   pressurizing the immiscible liquid located inside the sealed reservoir to detach the drop of liquid product from the outlet orifice of the injection tube and to push said drop inside the reception tube of said device.

15. Method for distributing according to claim 14, further comprising, prior to performing said injecting the liquid product and said pressurizing the immiscible liquid:
   facing the outlet orifice of the injection tube containing said liquid product and the inlet orifice of the reception tube each other.

16. Method for distributing according to claim 15, wherein said facing the outlet orifice and the inlet orifice each other is done by moving the injection tube containing said liquid product.

17. Method for distributing according to claim 15, wherein said facing the outlet orifice and the inlet orifice each other is done by moving the reception tube of said device.

18. Method for distributing according to claim 15, wherein said facing the outlet orifice and the inlet orifice each other is done through a control unit.

19. Method for distributing according to claim 14, further comprising, after said injecting the liquid product:
   pouring the liquid product from the injection tube towards the reception tube passing through the drop, which forms a liquid bridge between the two tubes.

* * * * *